US012765906B2

(12) United States Patent
Matsuo et al.

(10) Patent No.: US 12,765,906 B2
(45) Date of Patent: Oct. 20, 2026

(54) ENDOSCOPIC TREATMENT PORTION TRACTION MEMBER

(71) Applicants: JOKOH CO., LTD., Tokyo (JP); St. Marianna University School of Medicine, Kawasaki (JP); Seiko Packing Co., Ltd., Tokyo (JP)

(72) Inventors: Yasumasa Matsuo, Kawasaki (JP); Shuumei Hirai, Tokyo (JP); Hironobu Minai, Kawasakai (JP)

(73) Assignees: JOKOH CO., LTD., Tokyo (JP); St. Marianna University School of Medicine, Kawasaki (JP); Seiko Packing Co., Ltd., Tokyo (JP)

( * ) Notice: Subject to any disclaimer, the term of this patent is extended or adjusted under 35 U.S.C. 154(b) by 662 days.

(21) Appl. No.: 18/206,113

(22) Filed: Jun. 6, 2023

(65) Prior Publication Data

US 2023/0346409 A1 Nov. 2, 2023

Related U.S. Application Data

(63) Continuation of application No. PCT/JP2021/044793, filed on Dec. 6, 2021.

(30) Foreign Application Priority Data

Dec. 7, 2020 (JP) ................................ 2020-202679

(51) Int. Cl.

| | |
|---|---|
| ***A61B 17/08*** | (2006.01) |
| ***A61B 17/00*** | (2006.01) |
| ***A61B 17/29*** | (2006.01) |

(52) U.S. Cl.

CPC .................................... *A61B 17/29* (2013.01)

(58) Field of Classification Search

CPC ........... A61F 2230/0065; A61B 17/083; A61B 17/08; A61B 17/068; A61B 17/064;

(Continued)

(56) References Cited

U.S. PATENT DOCUMENTS

2007/0049967 A1* 3/2007 Sibbitt .................. A61B 17/10 606/213
2009/0221934 A1 9/2009 Kuhns et al.

(Continued)

FOREIGN PATENT DOCUMENTS

CN 211484702 U 9/2020
EP 3 689 254 A1 8/2020

(Continued)

OTHER PUBLICATIONS

International Search Report dated Feb. 1, 2022 in counterpart International Application No. PCT/JP2021/044793w/English translation.

(Continued)

*Primary Examiner* — Majid Jamialahmadi
(74) *Attorney, Agent, or Firm* — DLA Piper LLP (US)

(57) ABSTRACT

An endoscopic treatment portion traction member is gripped by forceps to be inserted into an endoscope and then inserted into a body, and is fixed to a tissue to be resected and pulls the tissue from a surrounding tissue. The endoscopic treatment portion traction member includes: an annular body; and, an outer tongue provided in a peripheral portion of the annular body and is gripped by forceps.

8 Claims, 17 Drawing Sheets

(58) Field of Classification Search
CPC .......... A61B 2017/081; A61B 17/0218; A61B 17/0682; A61B 17/11; A61B 2017/1103; A61B 2017/1107
See application file for complete search history.

(56) References Cited

U.S. PATENT DOCUMENTS

| | | | | |
|---|---|---|---|---|
| 2014/0364882 | A1* | 12/2014 | Tulleken | A61B 17/11 606/153 |
| 2014/0379004 | A1* | 12/2014 | Raybin | A61B 17/083 606/143 |
| 2018/0279869 | A1 | 10/2018 | Wales et al. | |
| 2022/0096088 | A1* | 3/2022 | Sato | A61B 90/39 |

FOREIGN PATENT DOCUMENTS

| | | | |
|---|---|---|---|
| JP | 2004-321482 | A | 11/2004 |
| JP | 2005-103107 | A | 4/2005 |
| JP | 2008-062004 | A | 3/2008 |
| JP | 2010-268865 | A | 12/2010 |
| JP | 2019-118718 | A | 7/2019 |
| JP | 2020-506029 | A | 2/2020 |
| WO | 2019/066084 | A1 | 4/2019 |

OTHER PUBLICATIONS

Written Opinion dated Feb. 1, 2022 in counterpart International Application No. PCT/JP2021/044793.
Extended European Search Report dated Sep. 17, 2024, of counterpart European Patent Application No. 21903377.6.

* cited by examiner

ENDOSCOPIC TREATMENT PORTION TRACTION MEMBER

TECHNICAL FIELD

This disclosure relates to an endoscopic treatment portion traction member. More specifically, this disclosure relates to a traction member for lifting the tissue to be resected from the surrounding tissue to assist in the resection of the tissue to be resected during endoscopic treatment.

BACKGROUND

Improvements in endoscope performance have allowed endoscopes to be used not only for examination of internal tissues but also for tissue sampling and even tissue resection recently. As an example of endoscopic surgery, endoscopic submucosal dissection (ESD) allows a tumor tissue (lesion site) of early-stage cancer that has developed on the mucosa within the digestive tract such as the colon to be minimally invasively resected.

In the ESD treatment, the lesion site to be resected is first identified. Next, saline or other solution is injected into the submucosal layer immediately below the lesion site, and the lesion to be resected is lifted from the surrounding tissue. Then, incision of the mucosa around the lesion site and dissection of the submucosal layer are performed. When the submucosal layer around the lesion site is incised and resected, the lifted lesion site is not sufficient to accurately incise the area around the lesion site in the limited field of view of the endoscope. Accordingly, the lesion site (and its surroundings) needs to be further lifted in the intestinal tract.

In lifting the lesion site, a traction member including clips that grip the tissue surface and the lesion site in the intestinal tract has been proposed (see, e.g., Japanese Laid-Open Patent Publication Nos. 2008-62004 and 2005-103107). However, the traction members proposed in JP2008-62004A and JP2005-103107A are complex in structure, and the overall size causes the traction member to be hard to be manipulated at the treatment site using forceps incorporated into an endoscope.

Accordingly, a simplified traction member with the clips separate from the traction member has been proposed (see Japanese Laid-Open Patent Publication No. 2019-118718). The traction member in JP2019-118718A is configured to have a plurality of interconnected rings, achieving a certain effect in hanging with the clips. Since the traction member in JP2019-118718A is configured to have a plurality of interconnected rings, however, the strength of the interconnected portions of the rings cannot be sufficiently maintained. Another problem is in the positions of the member at a time when the rings are bundled together and gripped by the forceps.

It could therefore be helpful to provide an endoscopic treatment portion traction member that satisfies ease of gripping the traction member by endoscopic forceps and ease of handling in the area to be treated.

SUMMARY

We thus provide an endoscopic treatment portion traction member where in improving the traction member that lifts the tissue to be resected from the surrounding tissue to assist in the resection of the tissue to be resected during endoscopic treatment, the ease of grasping the traction member with endoscopic forceps and the ease of handling it in the area to be treated are improved.

That is, in an example, an endoscopic treatment portion traction member is gripped by forceps inserted into an endoscope to be inserted into the body, and fixed to the tissue to be resected to pull the tissue to be resected from the surrounding tissue. The endoscopic treatment portion traction member included an annular body; an outer tongue provided in a peripheral portion of the annular body and gripped by the forceps.

The outer tongue may be provided at one or two locations in the peripheral portion of the annular body.

The outer tongue may include a tapered portion.

The tip end of the outer tongue may be chamfered in an arcuate shape.

The annular body may be circular in shape and the maximum length of the outer tongue may be 1/10 to 6/10 of the diameter of the peripheral portion of the circular annular body.

The annular body may be oval in shape, and the maximum length of the outer tongue may be 1/10 to 3/10 of the minor axis length of the peripheral portion of the oval-shaped annular body.

The annular body may be circular in shape and the diameter of the peripheral portion of the annular body may be 5 to 30 mm.

An inner tongue section may be provided in the inner circumferential portion of the annular body opposite the outer tongue.

The endoscopic treatment portion traction member may be formed from an elastic resin.

The outer tongue may include a tongue pore.

When the endoscopic treatment portion traction member is fixed to the tissue to be resected, the endoscopic treatment portion traction member may be suspended via a clip secured to the tissue to be resected.

Accordingly, the endoscopic treatment portion traction member, which is gripped by forceps inserted into the endoscope and inserted into the body, is fixed to the tissue to be resected to lift the tissue from the surrounding tissue. The member includes an annular body; and an outer tongue provided around the peripheral portion of the annular body and gripped by the forceps. This improves, during the treatment using the endoscope, the ease of gripping the traction member by the endoscopic forceps and the ease of handling in the area to be treated.

BRIEF DESCRIPTION OF THE DRAWINGS

Features, advantages, and technical and industrial significance of examples of our traction members will be described below with reference to the accompanying drawings, in which like numerals denote like elements.

DESCRIPTION OF THE REFERENCE NUMERALS

- 1, 1A, 1B, 1C, 2A, 2B, 2C, 2D, 3A, 3B, 3C, 4A, 4B, 4C, 5A, 5B, 1D, 2A1, 2B1, 2C1, 2D1, 3A1, 3B1, 3C1, 4A1, 4B1, 4C1, 5A1, 5B1: Endoscopic Treatment Portion Traction Member
- 10, 10*x*, 10*y*, 10*z*, 10*w*: Annular Body
- 11: Inner Circumferential Portion
- 12: Peripheral Portion
- 13: Installation Position
- 14: Tip End
- 15, 15*a*, 15*b*, 15*c*, 15*d*, 15*e*, 15*f*, 15*g*: Outer Tongue
- 16, 17: Tapered Portion
- 18: Inner Circular Portion
- 20: Forceps
- 21, 22: Forceps Jaws
- 25: Forceps Tip End
- 30: Endoscope
- 31: Insertion Port
- 32: Conduit
- 33: Opening
- 35: Electrocautery
- 36: Loop End
- 40: Tongue Pore
- 50: Colon
- 51: Mucosal Tissue

52: Inside of Intestinal Tract
55: Lesion Site (Tissue to be Resected)
60: Clips
85, 85*a*, 85*b*, 85*c*, 85*d*, 85*e*, 85*f*, 85*g*: Inner Tongue
D: Diameter of Peripheral Portion of Annular Body
L: Maximum Length of Tongue
E: Maximum Length of Tongue Pore

DETAILED DESCRIPTION

The endoscopic treatment portion traction member according to an example is directed to a member exclusively used during endoscopic submucosal dissection, which member is fixed to a tissue to be resected, and lifts and pulls the tissue from the surrounding tissue. Endoscopic submucosal dissection mainly targets the resection of tumor tissue (lesion site) of early-stage cancerous growths on the mucosa inside the digestive tract including the colon (such as rectum, S-colon, descending colon, transverse colon, ascending colon, cecum). Further, the endoscopic treatment portion traction member can be applied to any portion or organ into which an endoscope can be inserted. Examples may include the nasal cavity, cervix uteri, and uterine head. The endoscopic submucosal dissection will be described with reference to FIGS. 5A to 6.

Figure 1:
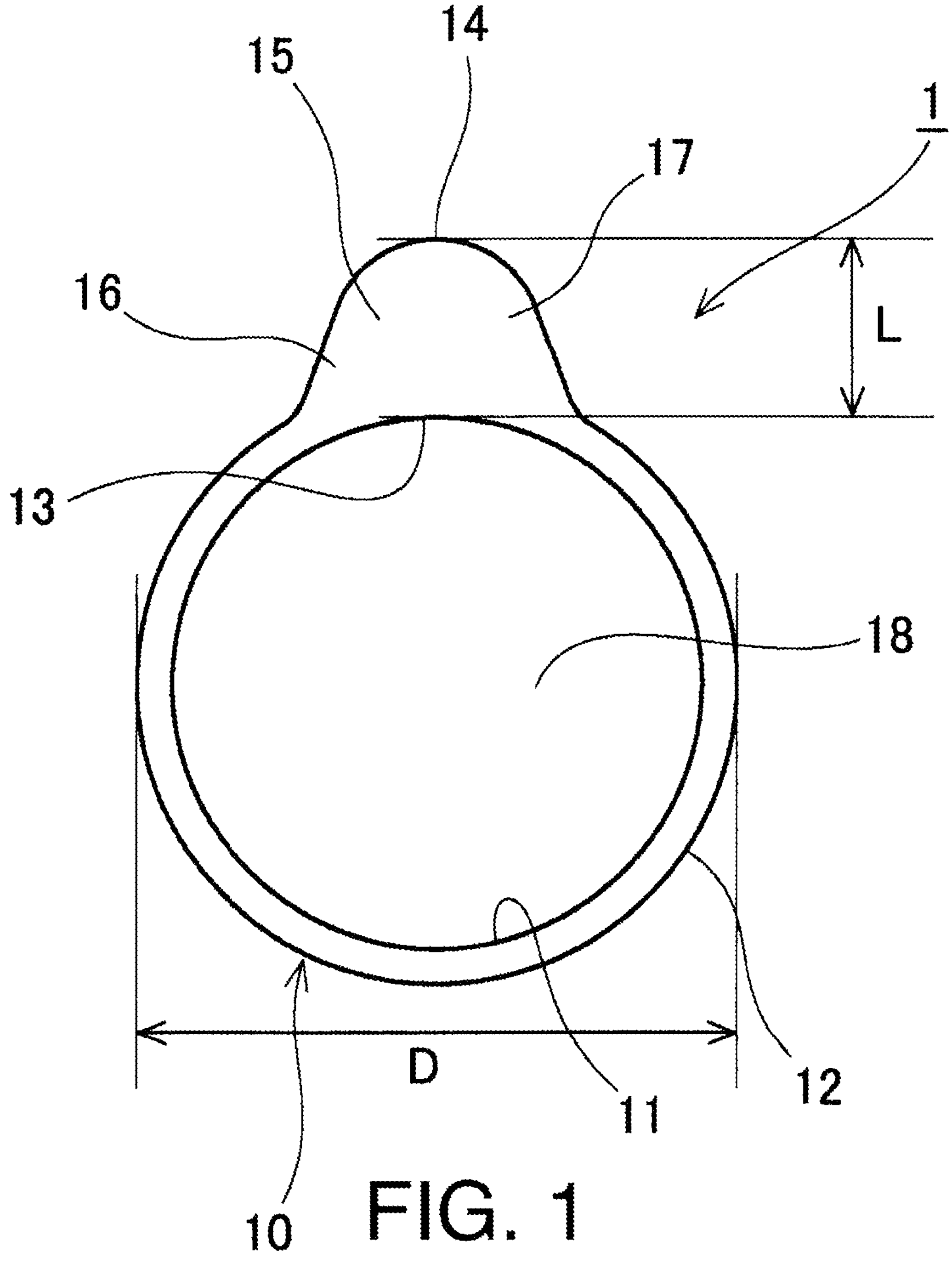
FIG. 1 is an overall plan view illustrating an endoscopic treatment portion traction member according to a first example.

FIG. 1 is an overall plan view of an endoscopic treatment portion traction member 1 according to a first example. The endoscopic treatment portion traction member 1 includes a circular annular body 10 and an outer tongue 15 protruding outward from the annular body 10. The annular body 10 is configured by an inner circumferential portion 11 and a peripheral portion 12, and an inner circular portion 18 is formed inside the annular body 10. The diameter (D) of the peripheral portion 12 of the circular annular body 10 is 5 to 30 mm, preferably 10 to 30 mm. As described below, the endoscopic treatment portion traction member 1 is inserted into the endoscope for treatment on the lesion site. The diameter is specified in consideration of the size at that time. The annular body 10 of the endoscopic treatment portion traction member 1 according to the example is circular. In addition to this, the annular body 10 can be oval-shaped.

In the endoscopic treatment portion traction member 1 according to the first example, the tongue 15 is provided at one location in the peripheral portion 12 of the annular body 10. The outer tongue 15 is gripped by forceps 20 (see FIGS. 2A to 3B, for example) that are inserted into the endoscope 30. In consideration of convenience of grasping, it may be desirable for the outer tongue to be present at various locations around the peripheral portion of the annular body. However, the endoscopic treatment portion traction member needs to pass through a narrow conduit of the endoscope. The extra outer tongue then becomes a resistance during the passage of the member through the conduit, hindering the smooth passage thereof. Accordingly, as in the endoscopic treatment portion traction member 1 according to the example, the outer tongue 15 is provided at one installation position 13 in the peripheral portion 12 of the annular body 10. In the second and other examples described below, the outer tongue is provided at two positions opposite to each other (180° orientation) of the peripheral portion 12. Even if the tongues are provided in the opposite positions, the resistance during the passage of the member through the conduit is reduced.

The maximum length (L) of the outer tongue 15 is 1/10 to 6/10, preferably 1/10 to 3/10 of the diameter of the peripheral portion 12 of the annular body 10. The length of the outer tongue 15 is acceptable if it is large enough to be gripped by the endoscopic forceps. If the outer tongue 15 is too small, the endoscopic forceps cannot easily grasp it. If it is significantly large, it may cause resistance to the passage in the endoscope through the conduit, which is undesirable.

As understood from the plan view in FIG. 1, the tip end 14 of the outer tongue 15 is chamfered to be arcuate. In addition, tapered portions 16, 17 are provided on the left and right sides of the outer tongue 15. The tapered portions 16, 17 taper from the installation position 13 side of the annular body 10 towards the tip end 14. The shapes are employed as features to reduce the resistance of the endoscopic treatment portion traction member 1 gripped by the forceps as it passes through the conduit of the endoscope.

Figure 2A:
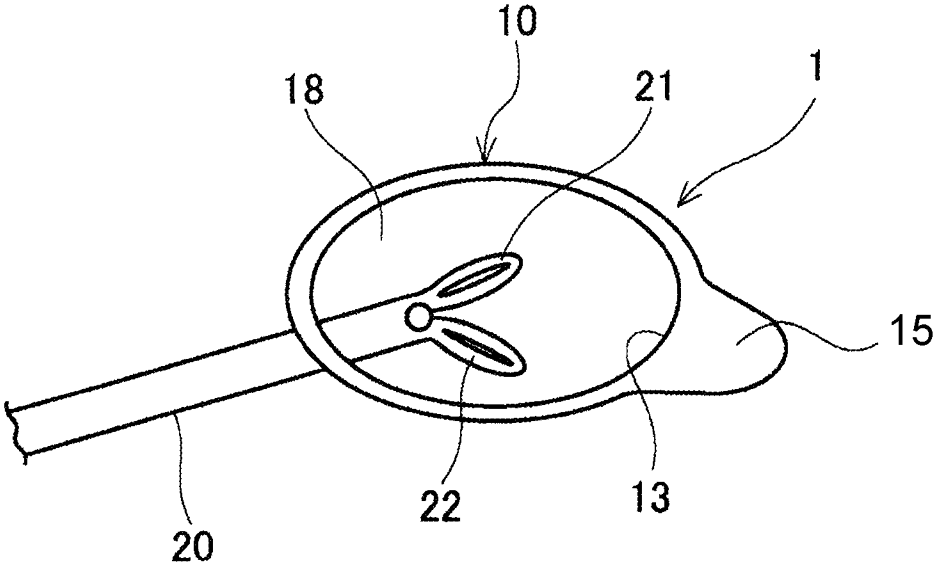
FIG. 2A is a diagram illustrating the endoscopic treatment portion traction member before it is gripped by forceps.

FIG. 2A illustrates the endoscopic treatment portion traction member 1 when it is gripped by the forceps 20 to be inserted into the endoscope. The forceps 20 are passed through the inside of the inner circular portion 18 for the installation position 13 of the annular body 10. Forceps jaws 21, 22 are provided at the tip ends of the forceps 20, and the opening and closing operations of the forceps jaws 21, 22 allow the object to be gripped. The forceps jaws 21, 22 in FIG. 2A are in the open state.

Figure 2B:
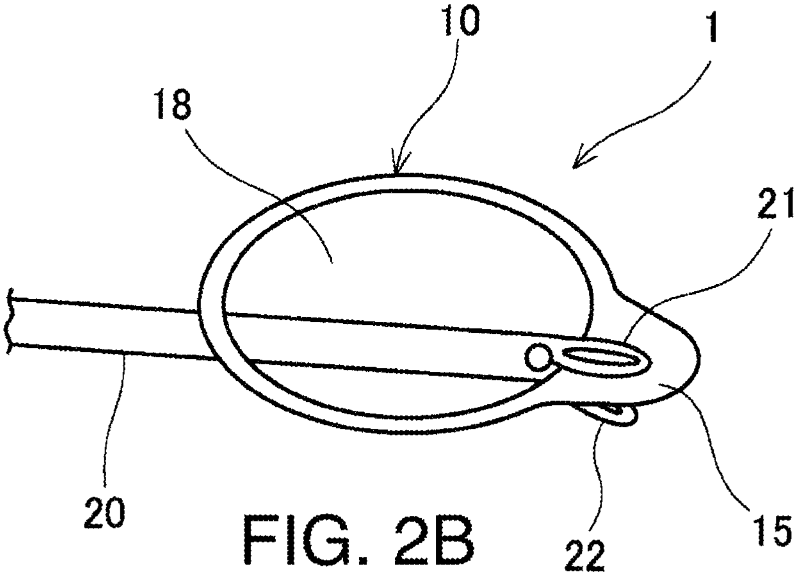
FIG. 2B is a diagram illustrating the endoscopic treatment portion traction member after it is gripped.

FIG. 2B illustrates the endoscopic treatment portion traction member 1 being gripped by the forceps 20. The forceps jaws 21, 22 of the forceps 20 are closed, and the outer tongue 15 is pinched by the forceps jaws 21, 22. The outer tongue 15 is a spreading plate portion of the annular body 10, facilitating the forceps jaws 21, 22 of the forceps 20 to grip the portion. In addition, the entire outer tongue 15 is easily retained in the grasped state. In this state, the endoscopic treatment portion traction member 1 is gripped by the forceps 20 and inserted into the endoscope.

Figure 3A:
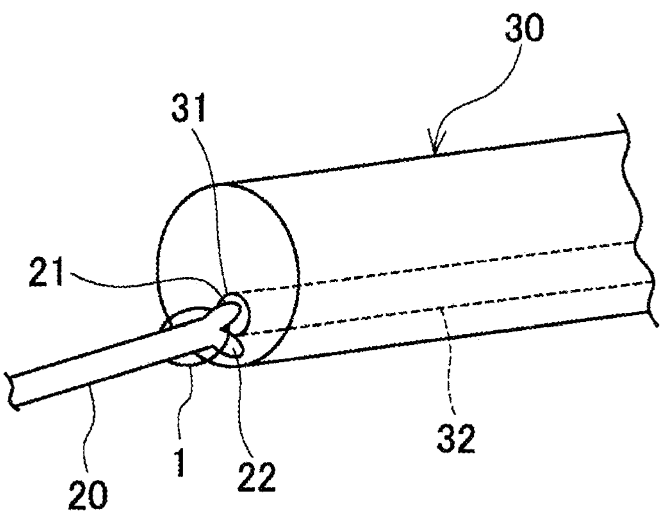
FIG. 3A is a diagram illustrating the endoscopic treatment portion traction member when it is inserted into an inside of an endoscope.

FIG. 3A illustrates the endoscopic treatment portion traction member 1 being inserted into the insertion port 31 of the endoscope 30 with the endoscopic treatment portion traction member 1 being held by the forceps 20 in FIG. 2B above. The endoscope 30 shown in the FIG. 3A has functions for endoscopic submucosal dissection and other procedures. Accordingly, the endoscope 30 includes a conduit 32 for inserting and removing the forceps for resection, suturing, and other procedures in addition to photographing the operating field.

Figure 3B:
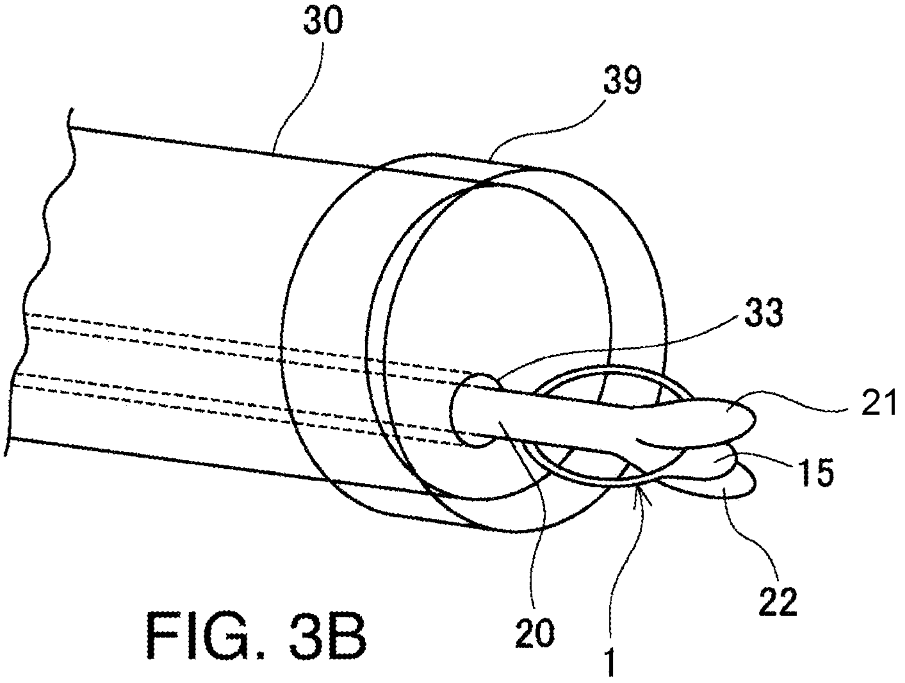
FIG. 3B is a diagram illustrating the endoscopic treatment portion traction member when it is exposed from the endoscope.

FIG. 3B illustrates the endoscopic treatment portion traction member 1 exposed through the opening 33 of the endoscope with the endoscopic treatment portion traction member 1 still held by the forceps 20. As disclosed in FIG. 1, since the endoscopic treatment portion traction member 1 is shaped to be subject to less resistance, it can be gripped by the forceps jaws 21, 22 and advanced through the conduit 32 without resistance. FIG. 3B shows a tip hood 39 of the endoscope 30.

Figure 4A:
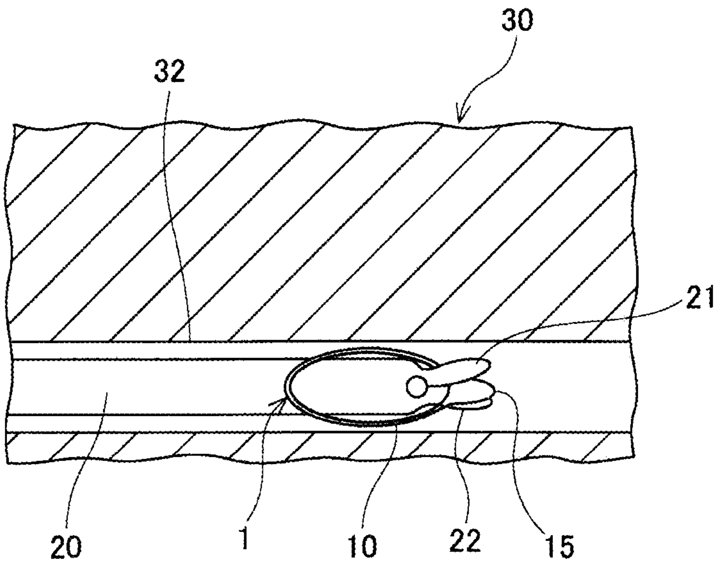
FIG. 4A is a vertical cross-sectional view illustrating the endoscopic treatment portion traction member when it is advanced into the inside of the endoscope.

FIG. 4A is a longitudinal sectional view of the endoscope in the longitudinal direction illustrating the endoscopic treatment portion traction member 1 being gripped by the forceps jaws 21, 22 of the forceps 20 and advanced in the conduit 32. The diameter of the body of the forceps 20 is less than the inner diameter of the conduit 32. In the endoscope shown in FIG. 4A, the inner diameter of the conduit 32 of the endoscope 30 is 3.2 mm and the diameter of the body of the forceps 20 is 2.2 mm, resulting in a gap of 1 mm in the diameter direction and 0.5 mm in real terms. In the endoscopic treatment portion traction member 1 according to this example, the difference between the inner circumferential portion 11 and the peripheral portion 12 of the annular body 10 (i.e., the width or thickness of the annular body 10) is approximately 0.3 to 0.5 mm.

Figure 4B:
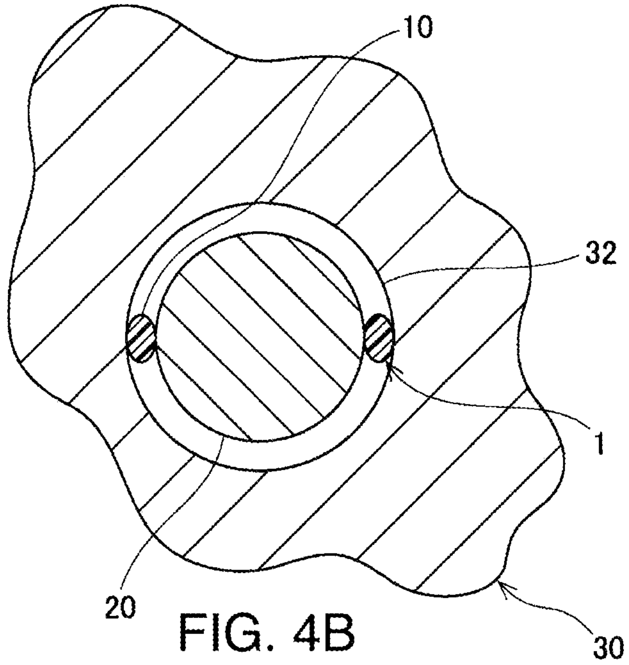
FIG. 4B is a horizontal cross-sectional view illustrating the endoscopic treatment portion traction member when it is advanced into the inside of the endoscope.

FIG. 4B is a cross-sectional view of the endoscope illustrating the portion of the endoscope that includes the forceps 20 and the endoscopic treatment portion traction member 1 gripped by the forceps 20. The annular body 10 of the endoscopic treatment portion traction member 1 in which the outer tongue 15 is gripped by the forceps jaws 21, 22 of the forceps 20 extends in the conduit 32 of the endoscope 30 in accordance with the direction of travel of the forceps 20. As mentioned above, the width (thickness) of the annular body 10 of the endoscopic treatment portion traction member 1 according to this example is narrower than the gap between the conduit 32 of the endoscope 30 and the forceps 20, allowing the endoscopic treatment portion traction member 1 to pass inside the conduit 32.

Figure 5A:
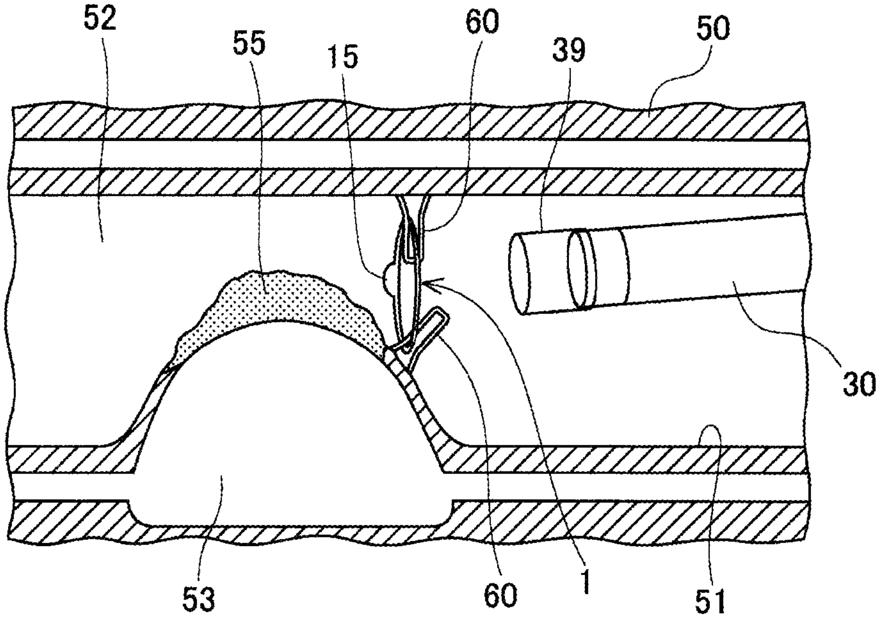
FIG. 5A is a first schematic diagram illustrating an endoscopic submucosal dissection.

As understood from the previous description, the endoscopic treatment portion traction member 1 according to this example is required to have tensile strength as well as elasticity and flexibility since it is used for traction applications. The elasticity and flexibility are properties required for the forceps 20 to deform in shape and be subject to less resistance when the forceps 20 are moved in and out of the conduit 32 of the endoscope 30. In addition, as shown in FIGS. 5A to 6 below, the endoscopic treatment portion traction member 1 is suspended by clips 60. The endoscopic treatment portion traction member 1 then pulls the clips together. In this example, the material cannot serve as a traction member since it is easily torn when it is pulled by the suspension.

Accordingly, the endoscopic treatment portion traction member 1 is formed by molding an elastic resin. Specifically, the resin may include polypropylene with elastomer components, polyvinyl chloride, urethane resin, and even silicone resin. Especially, silicone resin has excellent corrosion resistance and high stability as a medical material, and thus is desirable in consideration of its applications for treatment in the body. Injection molding, cast molding, or other appropriate methods are used to mold the silicone resin to achieve the endoscopic treatment portion traction member 1.

FIGS. 5A to 6 are schematic diagrams illustrating the form in which the endoscopic treatment portion traction member 1 according to this example is used in endoscopic submucosal dissection. FIGS. 5A to 6 illustrate a colon 50 as an organ, and the endoscope 30 is inserted through the anus (not shown). FIGS. 5A to 6 illustrate the form in which the lesion site 55 (tumor) in the mucosal tissue 51 on the surface of the colon 50 is resected from the surrounding mucosal tissue 51 as the tissue to be resected.

In FIG. 5A, a prior visual inspection of the mucosal tissue 51 on the surface of the colon 50 and the inside 52 of the intestinal tract by the endoscope 30 checks the operating field in which the lesion site 55 (tissue to be resected) is present. Saline 53 is injected directly under the lesion site 55 (below the mucosal tissue 51), and the lesion site 55 is lifted from the surrounding mucosal tissue 51. At this time, the clip 60 is inserted into the lesion site 55 through the endoscope 30. The other clip 60 is also inserted into the mucosal tissue 51 on the surface of the colon 50 opposite the clip 60 on the side of the lesion site 55.

As shown in FIG. 5A, the endoscopic treatment portion traction member 1 is then suspended between the two clips 60, 60, which are inserted into the inside 52 of the intestinal tract. For the suspension of the endoscopic treatment portion traction member 1 between the clips 60, the annular body 10 of the endoscopic treatment portion traction member 1 is inserted into a cut (not shown) in each clip 60 and pushed into the clip 60. This operation is performed through the forceps 20 (forceps jaws 21, 22) inserted into the endoscope 30. The lesion site 55 (tissue to be resected) lifted from the mucosal tissue 51 by the injection of the saline 53 is moderately lifted and maintained by the endoscopic treatment portion traction member 1 connecting the clips 60, 60.

Figure 5B:
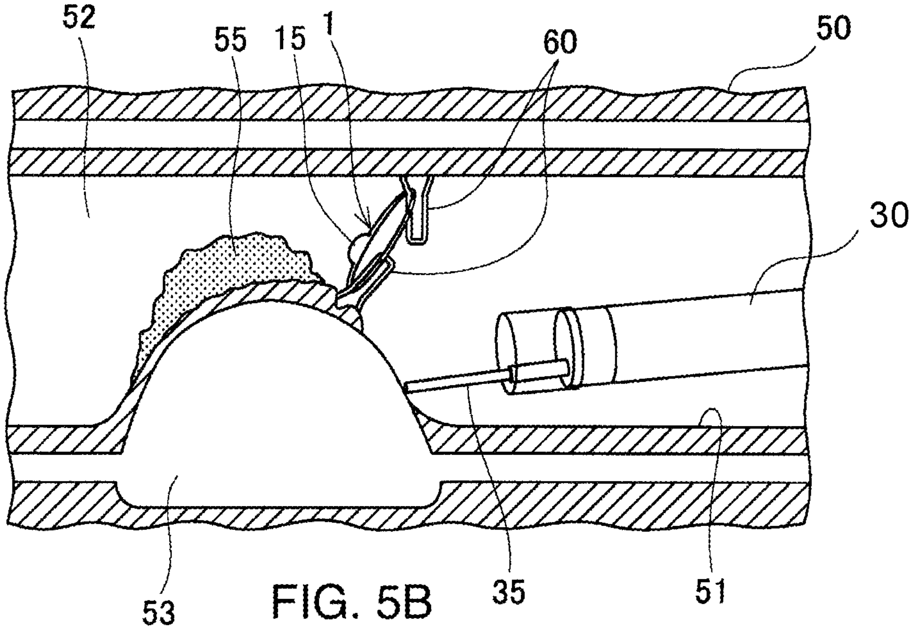
FIG. 5B is a second schematic diagram illustrating the endoscopic submucosal dissection.
Figure 6:
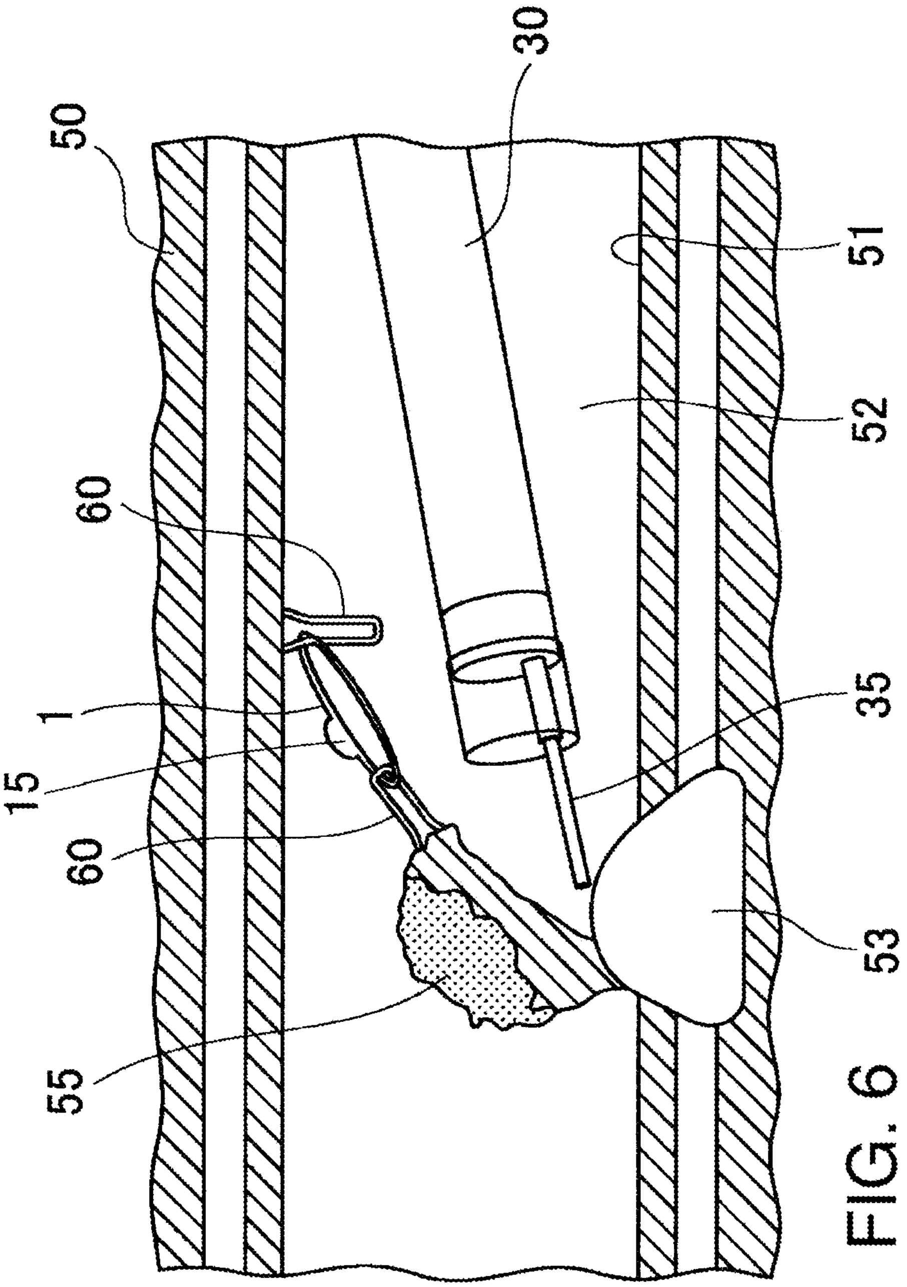
FIG. 6 is a third schematic diagram illustrating the endoscopic submucosal dissection.

In FIG. 5B, the mucosal tissue 51 around the lesion site 55 is gradually resected by the electrocautery 35 protruding from the endoscope 30. At this time, the lesion site 55 is lifted by the endoscopic treatment portion traction member 1, facilitating the electrocautery 35 to be applied to the target mucosal tissue 51.

FIG. 6 illustrates the final stage of further performed resection of the lesion site 55 (tissue to be resected). In FIG. 6, the suspension of the endoscopic treatment portion traction member 1 has been adjusted, and the lesion site 55 continues to be resected by the electrocautery 35. As understood from the disclosure and illustration of FIGS. 5A to 6, the endoscopic treatment portion traction member 1 is a traction aid for assisting the traction through the clips.

In addition to the endoscopic treatment portion traction member according to the first example that has been illustrated and described so far, the endoscopic treatment portion traction members according to the second through fourteenth examples will also be described with reference to FIGS. 7A to 9C.

Figure 7A:
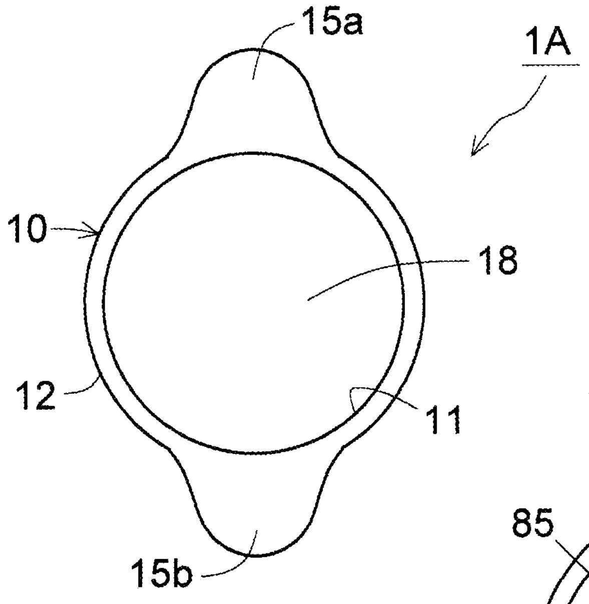
FIG. 7A is an overall plan view illustrating an endoscopic treatment portion traction member according to a second example.

The endoscopic treatment portion traction member 1A according to the second example in FIG. 7A includes two outer tongues 15*a* and 15*b* at 1800 opposite positions of the peripheral portion 12 of the circular annular body 10. In the endoscopic treatment portion traction member 1A, both the outer tongues 15*a* and 15*b* are more easily gripped by the forceps.

Figure 7B:
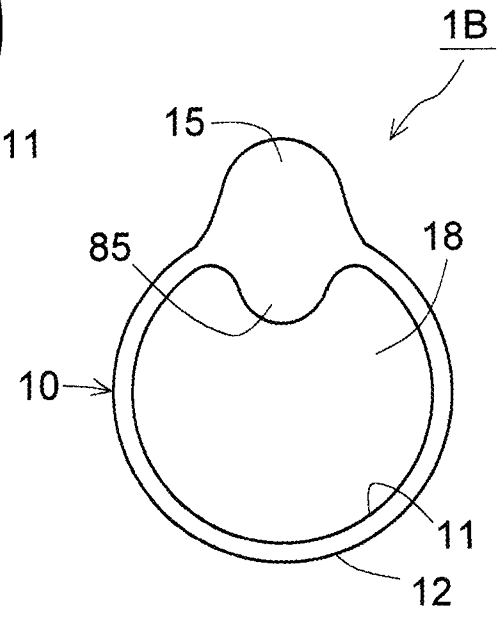
FIG. 7B is an overall plan view illustrating an endoscopic treatment portion traction member according to a third example.

The endoscopic treatment portion traction member 1B according to the third example in FIG. 7B includes an outer tongue 15 in the peripheral portion 12 of the circular annular body 10 and an inner tongue 85 in the inner circumferential portion 11 of the annular body 10 opposite the outer tongue 15. The inner tongue 85 is provided to be more easily grasped by the forceps.

Figure 7C:
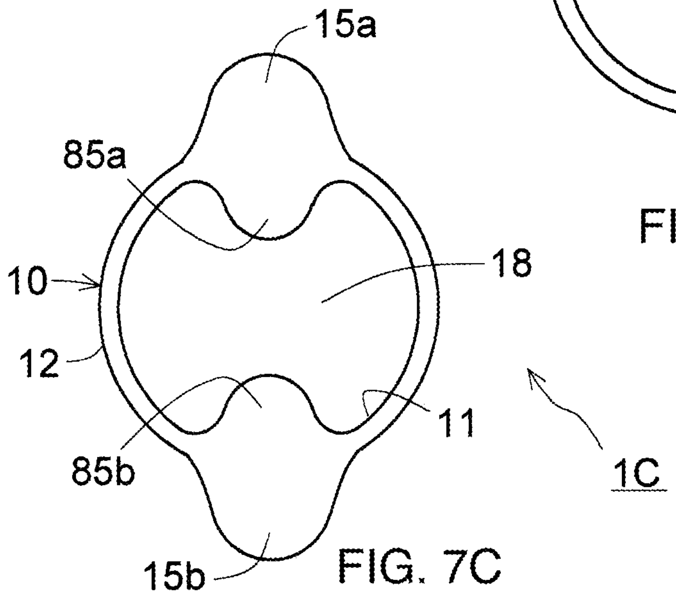
FIG. 7C is an overall plan view illustrating an endoscopic treatment portion traction member according to a fourth example.

The endoscopic treatment portion traction member 1C according to the fourth example in FIG. 7C includes two outer tongues 15*a* and 15*b* at 1800 opposite positions of the peripheral portion 12 of the circular annular body 10. Inner tongues 85*a* and 85*b* are further provided in the inner circumferential portion 11 at opposite positions of both the outer tongues 15*a* and 15*b*. The tongues at both ends allow the endoscopic treatment portion traction member to be easily gripped.

Each endoscopic treatment portion traction member in FIGS. 8A to 8D includes an oval-shaped annular body 10*x*. The ratio of the minor axis to the major axis of the oval-shaped annular body 10*x* is appropriate. In consideration of practicality, the ratio of the minor axis to the major axis (minor axis:major axis) is 1:1.1 to 1:4. The maximum length of the outer tongue 15 (15*a*, 15*b*) is in the range of 1⁄10 to 3⁄10 of the minor axis length of the peripheral portion 12 of the oval-shaped annular body 10*x*. The same may be applied to each of the forms in FIGS. 8A to 8D.

Figure 8A:
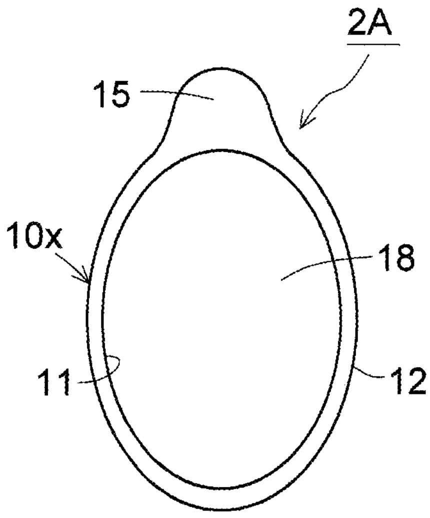
FIG. 8A is an overall plan view illustrating an endoscopic treatment portion traction member according to a fifth example.

The endoscopic treatment portion traction member 2A according to the fifth example in FIG. 8A includes an oval-shaped annular body 10*x*, and an outer tongue 15 is provided at one location in the peripheral portion 12 of the annular body 10*x*. The oval shape of the annular body allows the direction of the endoscopic treatment portion traction member to be visually easily determined when it is gripped by the forceps or inserted into the endoscope.

Figure 8B:
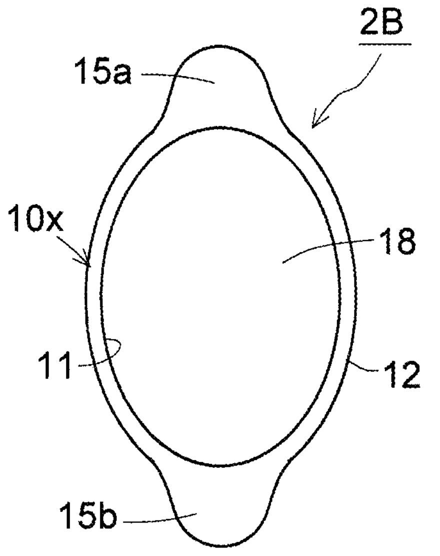
FIG. 8B is an overall plan view illustrating an endoscopic treatment portion traction member according to a sixth example.

The endoscopic treatment portion traction member 2B according to the sixth example in FIG. 8B includes two outer tongues 15 at 1800 opposite positions of the peripheral portion 12 of the oval-shaped annular body 10*x*. In the endoscopic treatment portion traction member 2B, both the outer tongues 15*a* and 15*b* are more easily gripped by the forceps.

Figure 8C:
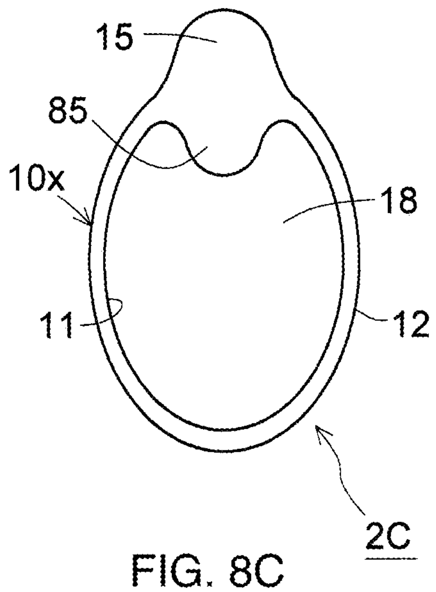
FIG. 8C is an overall plan view illustrating an endoscopic treatment portion traction member according to a seventh example.

The endoscopic treatment portion traction member 2C according to the seventh example in FIG. 8C includes an outer tongue 15 in the peripheral portion 12 of the oval-shaped annular body 10 and an inner tongue 85 in the inner circumferential portion 11 of the annular body 10*x* opposite the outer tongue 15. The inner tongue 85 is provided to be more easily grasped by the forceps.

Figure 8D:
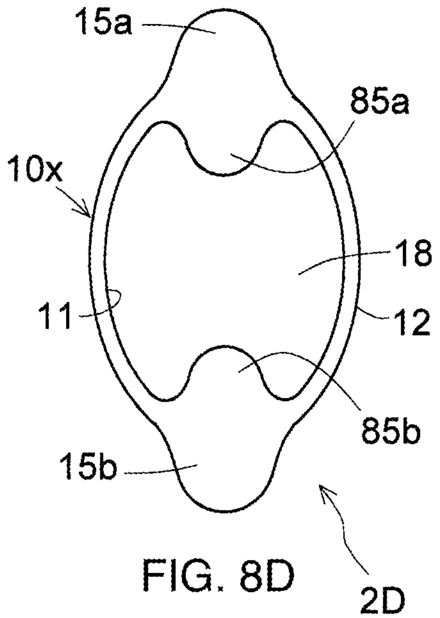
FIG. 8D is an overall plan view illustrating an endoscopic treatment portion traction member according to an eighth example.

The endoscopic treatment portion traction member 2D according to the eighth example in FIG. 8D includes two outer tongues 15*a* and 15*b* at 180° opposite positions of the peripheral portion 12 of the oval-shaped annular body 10*x*. Inner tongues 85*a* and 85*b* are further provided in the inner circumferential portion 11 at opposite positions of both the outer tongues 15*a* and 15*b*. The tongues at both ends allow the endoscopic treatment portion traction member to be easily gripped.

Figure 9A:
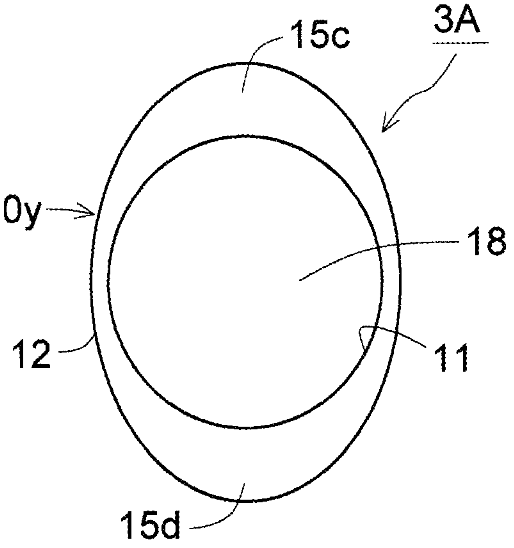
FIG. 9A is an overall plan view illustrating an endoscopic treatment portion traction member according to a ninth example.
Figure 9B:
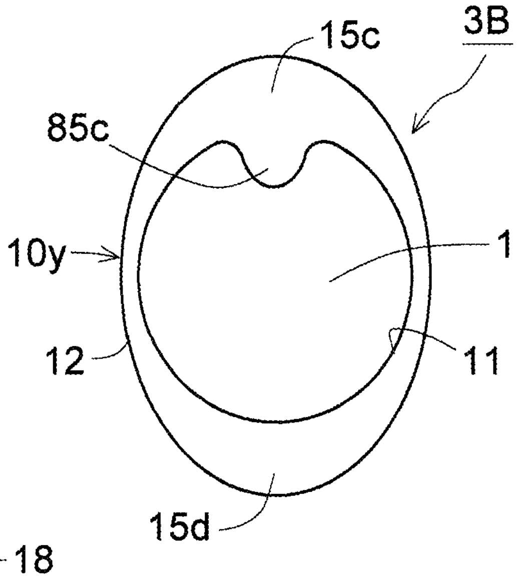
FIG. 9B is an overall plan view illustrating an endoscopic treatment portion traction member according to a tenth example.
Figure 9C:
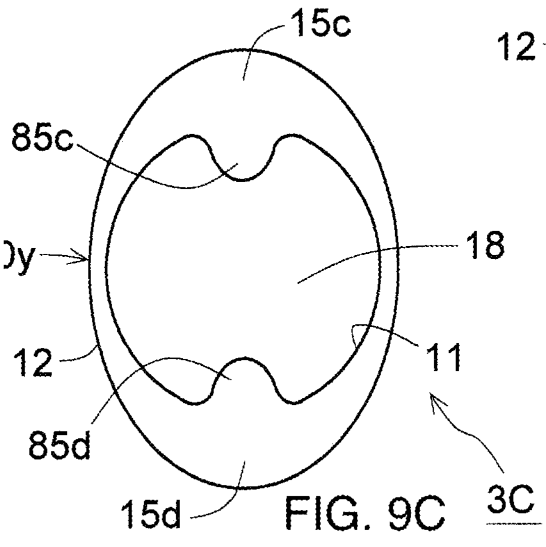
FIG. 9C is an overall plan view illustrating an endoscopic treatment portion traction member according to an eleventh example.

Each endoscopic treatment portion traction member in FIGS. 9A to 9C is an oval-shaped annular body 10*y*, and a variation of FIGS. 8A to 8D. That is, the outer tongue 15 (15*c*, 15*d*) is not protruding but is incorporated into a part of the oval-shaped annular body 10*y*. In FIGS. 9A to 9C, the ratio of the minor axis to the major axis of the oval-shaped annular body 10*y* is also appropriate. In consideration of practicality, the ratio of the minor axis to the major axis (minor axis:major axis) is 1:1.1 to 1:4. The maximum length of the outer tongue 15 (15*c*, 15*d*) is in the range of 1/10 to 3/10 of the minor axis length of the peripheral portion 12 of the oval-shaped annular body 10*y*. The same may be applied to each of the forms in FIGS. 9A to 9C.

In the endoscopic treatment portion traction member 3A according to the ninth example in FIG. 9A, the width of the outer tongues 15*c* and 15*d* is extended and integrated with the oval-shaped annular body 10*y*. The same may be applied to the other forms in FIGS. 9B and 9C. The endoscopic treatment portion traction member 3A has less resistance in terms of shape, facilitating the insertion into the endoscope.

The endoscopic treatment portion traction member 3B according to the tenth example in FIG. 9B includes outer tongues 15*c* and 15*d* with the widths extended at opposite positions in the peripheral portion 12 of the oval-shaped annular body 10*y* and an inner tongue 85*c* in the inner circumferential portion 11 of the annular body 10*y* opposite the outer tongue 15*c*. The inner tongue 85 is provided to be more easily grasped by the forceps.

The endoscopic treatment portion traction member 3C according to the eleventh example in FIG. 9C includes outer tongues 15*c* and 15*d* with the widths extended at opposite positions in the peripheral portion 12 of the oval-shaped annular body 10*y* and inner tongues 85*c* and 85*d* in the inner circumferential portion 11 of the annular body 10*y* opposite the outer tongues 15*c* and 15*d*. The inner tongues 85*c* and 85*d* facilitate gripping by the forceps from both directions.

Figure 10A:
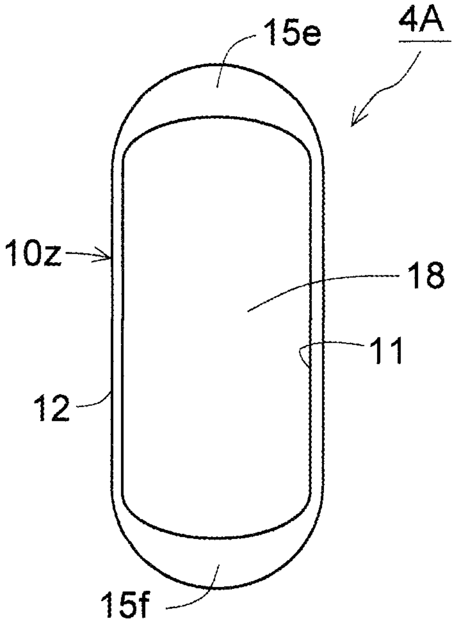
FIG. 10A is an overall plan view illustrating an endoscopic treatment portion traction member according to a twelfth example.
Figure 10B:
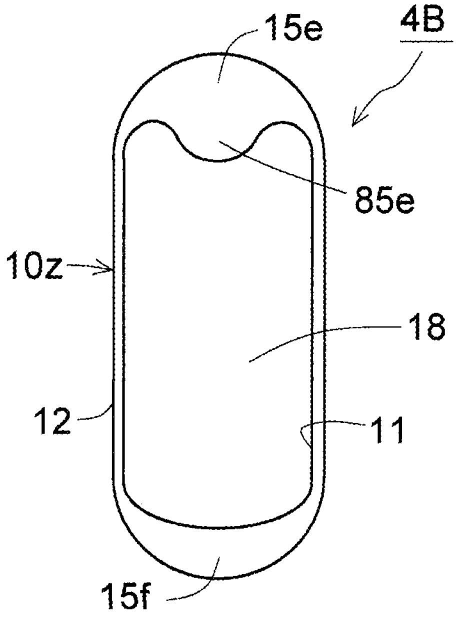
FIG. 10B is an overall plan view illustrating an endoscopic treatment portion traction member according to a thirteenth example.
Figure 10C:
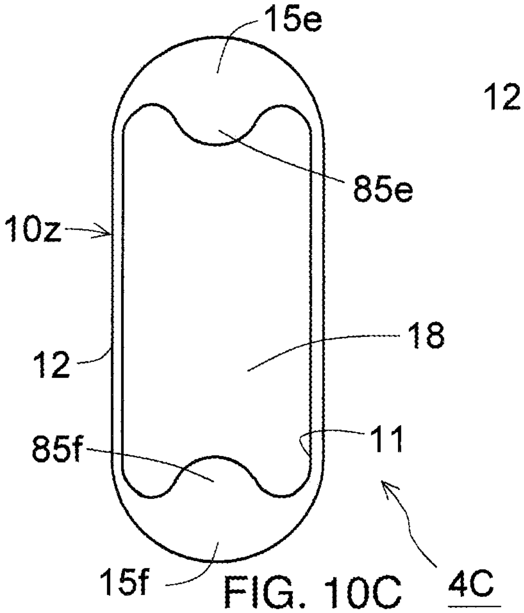
FIG. 10C is an overall plan view illustrating an endoscopic treatment portion traction member according to a fourteenth example.

Each endoscopic treatment portion traction member in FIGS. 10A to 10C is a deformed oval-shaped annular body 10*z*, and includes a shape referred to as a stadium track, for example. In FIGS. 10A to 10C, the outer tongues 15*e*, 15*f* are not protruding but are incorporated into a part of the oval-shaped annular body 10*z*. In FIGS. 10A to 10C, the ratio of the minor axis to the major axis of the annular body 10*z* is also appropriate. In consideration of practicality, the ratio of the minor axis to the major axis (minor axis:major axis) is 1:1.1 to 1:4. The maximum length of the outer tongue 15 (15*e*, 15*f*) is in the range of 1/10 to 3/10 of the minor axis length of the peripheral portion 12 of the oval-shaped annular body 10*z*. The same may be applied to each of the forms in FIGS. 10A to 10C.

In the endoscopic treatment portion traction member 4A according to the twelfth example in FIG. 10A, the width of the outer tongues 15*e* and 15*f* is extended and integrated with the oval-shaped annular body 10*z*. The same may be applied to the other forms in FIGS. 10B and 10C. The endoscopic treatment portion traction member 4A has less resistance in terms of shape, facilitating the insertion into the endoscope.

The endoscopic treatment portion traction member 4B according to the thirteenth example in FIG. 10B includes outer tongues 15*e* and 15*f* with the widths extended at opposite positions in the peripheral portion 12 of the oval-shaped annular body 10*z* and an inner tongue 85*e* in the inner circumferential portion 11 of the annular body 10*z* opposite the outer tongue 15*e*. The inner tongue 85*e* is provided to be more easily grasped by the forceps.

The endoscopic treatment portion traction member 4C according to the fourteenth example in FIG. 10C includes outer tongues 15*e* and 15*f* with the widths extended at opposite positions in the peripheral portion 12 of the oval-shaped annular body 10*z* and inner tongues 85*e* and 85*f* in the inner circumferential portion 11 of the annular body 10*z* opposite the outer tongues 15*e* and 15*f* The inner tongues 85*e* and 85*f* facilitate gripping by the forceps from both directions.

Figure 11A:
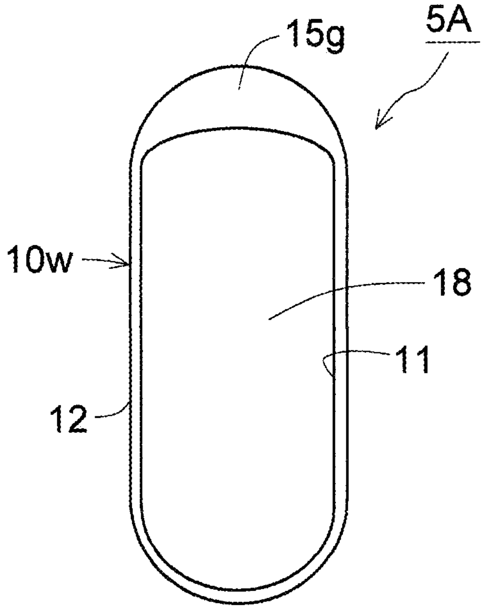
FIG. 11A is an overall plan view illustrating an endoscopic treatment portion traction member according to a fifteenth example.
Figure 11B:
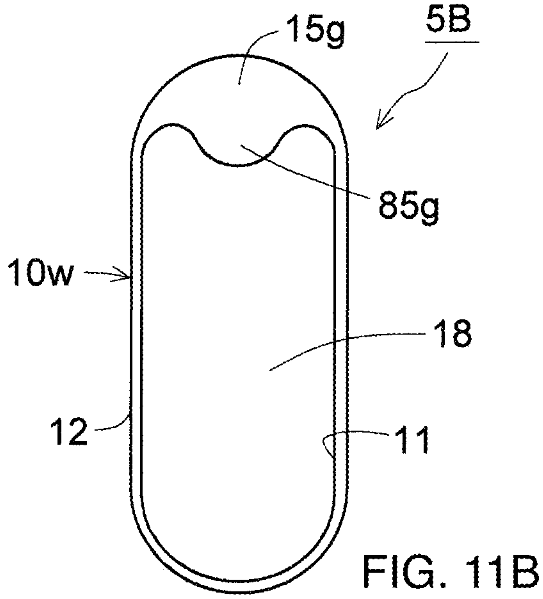
FIG. 11B is an overall plan view illustrating an endoscopic treatment portion traction member according to a sixteenth example.

Each endoscopic treatment portion traction member in FIGS. 11A and 11B is a deformed oval-shaped annular body 10*w*, and corresponds to a variation of the annular body 10*z* (with the shape referred to as a stadium track, for example) in FIGS. 10A to 10C. The outer tongue 15*g* is located at only one position, and is not protruding, but rather is incorporated into a portion of the oval-shaped annular body 10*w*. In FIGS. 11A and 11B, the ratio of the minor axis to the major axis of the annular body 10*w* is also appropriate. In consideration of practicality, the ratio of the minor axis to the major axis (minor axis:major axis) is 1:1.1 to 1:4. The maximum length of the outer tongue 15 (15*g*) is in the range of 1/10 to 3/10 of the minor axis length of the peripheral portion 12 of the oval-shaped annular body 10*w*. The same may be applied to each of the forms in FIGS. 11A and 11B.

In the endoscopic treatment portion traction member 5A according to the fifteenth example in FIG. 11A, the width of the outer tongue 15*g* is extended and integrated with the oval-shaped annular body 10*w*. The same may be applied to the other form in FIG. 11B. The endoscopic treatment portion traction member 5A has less resistance in terms of shape, facilitating the insertion into the endoscope. The arrangement of the outer tongue 15*g* also determines the directionality of the endoscopic treatment portion traction member 5A at a time when it is gripped by the forceps.

In the endoscopic treatment portion traction member 5B according to the sixteenth example in FIG. 11B, the width of the outer tongue 15*g* is extended and integrated with the oval-shaped annular body 10*w*. Further, an inner tongue 85*g* is provided in the inner circumferential portion 11 of the annular body 10*w* opposite the outer tongue 15*g*. The inner tongue 85*g* is provided to be more easily grasped by the forceps. In the same manner, the arrangement of the outer tongue 15*g* determines the directionality of the endoscopic treatment portion traction member 5A at a time when it is gripped by the forceps.

Figure 12A:
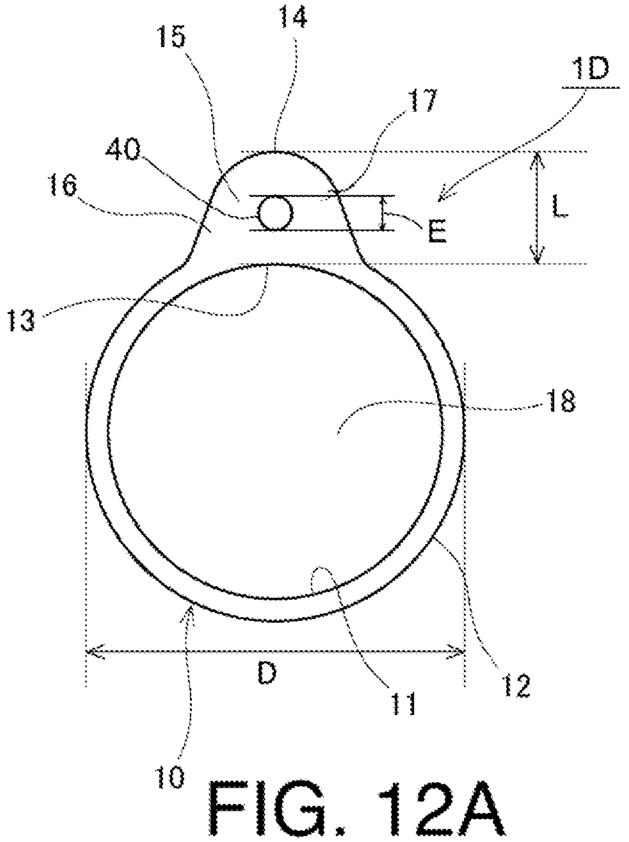
FIG. 12A is an overall plan view illustrating an endoscopic treatment portion traction member according to a seventeenth example.
Figure 12B:
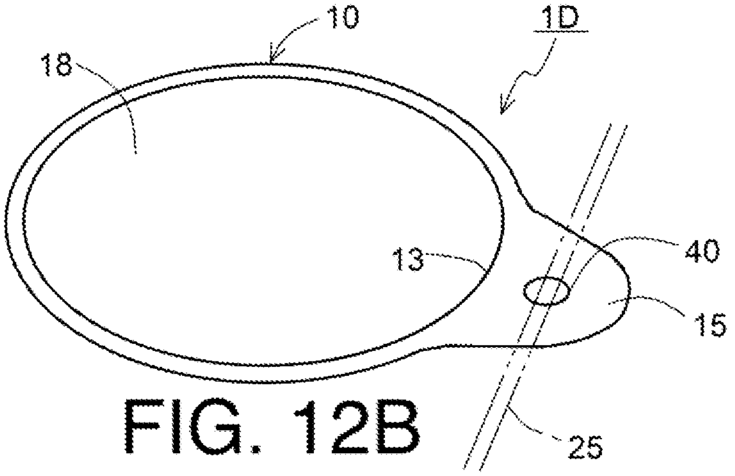
FIG. 12B is a perspective view illustrating the endoscopic treatment portion traction member when forceps are inserted through the endoscopic treatment portion traction member.

For each of the endoscopic treatment portion traction members illustrated in detail in FIGS. 1 through 11B, a tongue pore may also be formed into the outer tongue. FIG. 12A is a plan view of an endoscopic treatment portion traction member 1D according to the seventeenth example. The outer tongue 15 of the endoscopic treatment portion traction member 1D is perforated (formed therethrough) with a tongue pore 40. As shown in a perspective view in FIG. 12B, the forceps tip end 25 of forceps with a form different from that of the forceps 20 (see FIGS. 2A to 4B) is inserted into the tongue pore 40. The forceps tip end 25 shown in the FIG. 12B corresponds to a thin rod-shaped member and is illustrated in part. Two forceps tip ends 25 can be crossed (not shown). As described above, the endoscopic treatment portion traction member 1D is hooked to the forceps tip end 25 through the tongue pore 40. In addition, if needed, the forceps tip end 25 side may include a plastic annular spacer member (not shown) to protect the contact area with the tongue pore 40. This is to protect the metal forceps tip end 25 and the plastic endoscopic treatment portion traction member 1D from damage due to wear.

The tongue pore 40 may have an opening large enough to ensure the insertion of the forceps tip end 25. The maximum length (E) of the tongue pore 40 is specified in the range of $0.5/10$ to $2/10$, preferably $1/10$ to $2/10$ of the diameter of the peripheral portion 12 of the annular body 10. Insertion of the forceps tip end 25 into the tongue pore 40 is less smooth. In addition, if the size is considerably large, the connection portion between the outer tongue 15 and the annular body 10 is likely to decrease, resulting in a reduction in strength. For example, in the endoscopic treatment portion traction member 1D according to the seventeenth example, the diameter (D) of the peripheral portion 12 of the annular body 10 is 10 mm and the maximum length (E) of the tongue pore 40 is 1.5 mm ($1.5/10$ of the diameter of the peripheral portion of the annular body).

The formation of the tongue pore in the outer tongue may be applied to any of the endoscopic treatment portion traction members according to the second to sixteenth examples disclosed in FIGS. 7A to 111B. Therefore, each endoscopic treatment portion traction member with a tongue pore in the outer tongue is shown as in FIGS. 13A to 17B. Since the configuration other than the tongue pore 40 is not changed in each endoscopic treatment portion traction member, the description thereof is omitted mainly as an illustration.

Figure 13A:
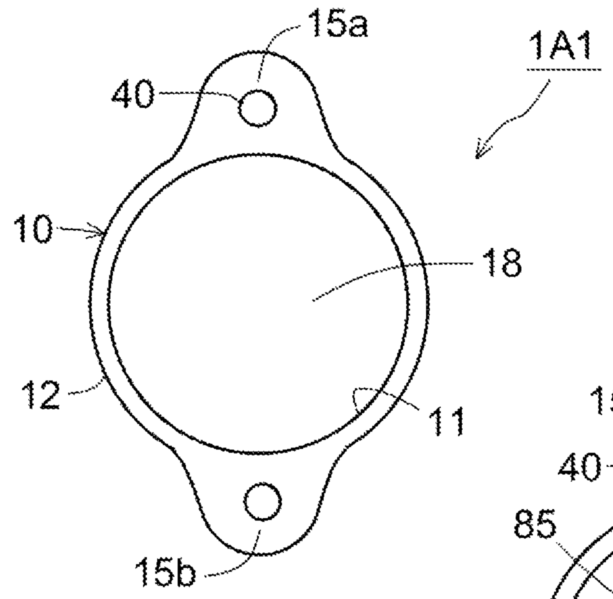
FIG. 13A is an overall plan view illustrating an endoscopic treatment portion traction member according to an eighteenth example.
Figure 13B:
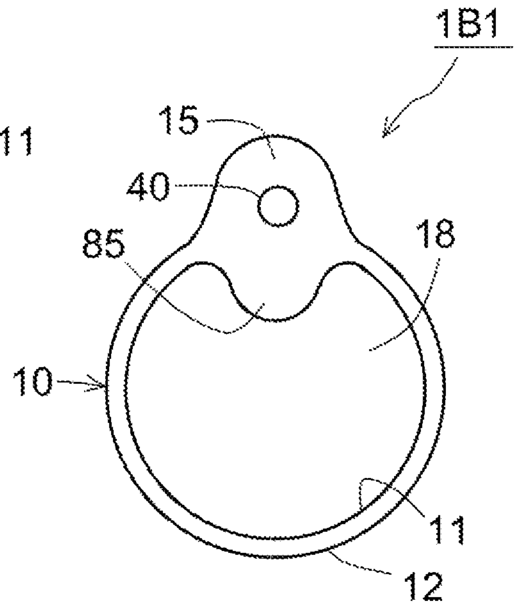
FIG. 13B is an overall plan view illustrating an endoscopic treatment portion traction member according to a nineteenth example.
Figure 13C:
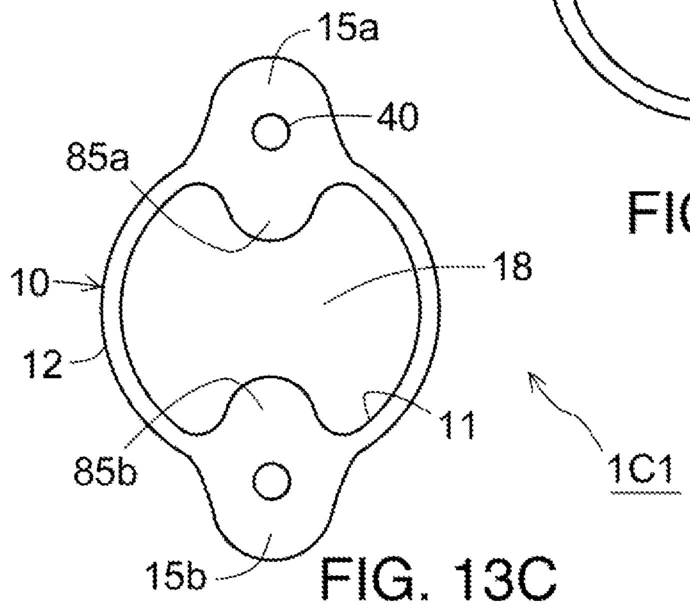
FIG. 13C is an overall plan view illustrating an endoscopic treatment portion traction member according to a twentieth example.

FIG. 13A illustrates an endoscopic treatment portion traction member 1A1 according to the eighteenth example, FIG. 13B illustrates an endoscopic treatment portion traction member 1B1 according to the nineteenth example, and FIG. 13C illustrates an endoscopic treatment portion traction member 1C1 according to the twentieth example. The endoscopic treatment portion traction members 1A1, 1B1, and 1C1 are capable of accommodating both the gripping of the outer tongue 15 by the forceps 20 or the insertion of the forceps tip end 25 into the tongue pore 40.

Figure 14A:
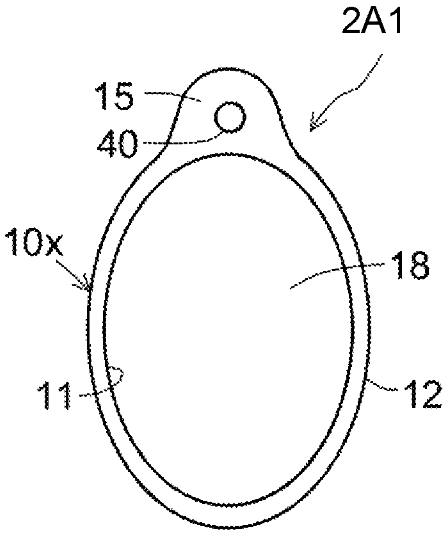
FIG. 14A is an overall plan view illustrating an endoscopic treatment portion traction member according to a twenty-first example.
Figure 14B:
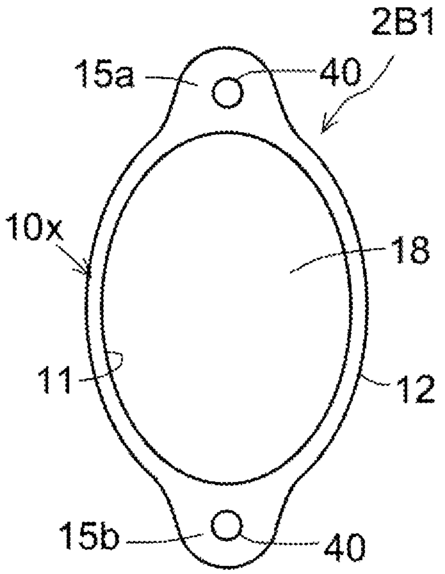
FIG. 14B is an overall plan view illustrating an endoscopic treatment portion traction member according to a twenty-second example.
Figure 14C:
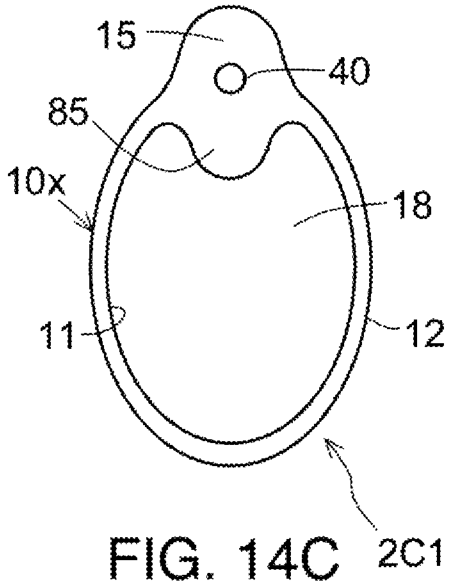
FIG. 14C is an overall plan view illustrating an endoscopic treatment portion traction member according to a twenty-third example.
Figure 14D:
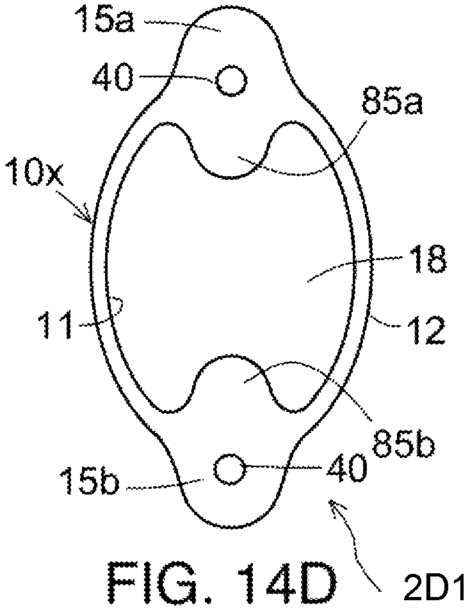
FIG. 14D is an overall plan view illustrating an endoscopic treatment portion traction member according to a twenty-fourth example.

FIG. 14A illustrates an endoscopic treatment portion traction member 2A1 according to the twenty-first example, FIG. 14B illustrates an endoscopic treatment portion traction member 2B1 according to the twenty-second example, FIG. 14C illustrates an endoscopic treatment portion traction member 2C1 according to the twenty-third example, and FIG. 14D illustrates an endoscopic treatment portion traction member 2D1 according to the twenty-fourth example. Even the endoscopic treatment portion traction members 2A1, 2B1, 2C1, and 2D1 with oval-shaped annular bodies are capable of accommodating both the gripping of the outer tongue 15 by the forceps 20 or the insertion of the forceps tip end 25 into the tongue pore 40.

Figure 15A:
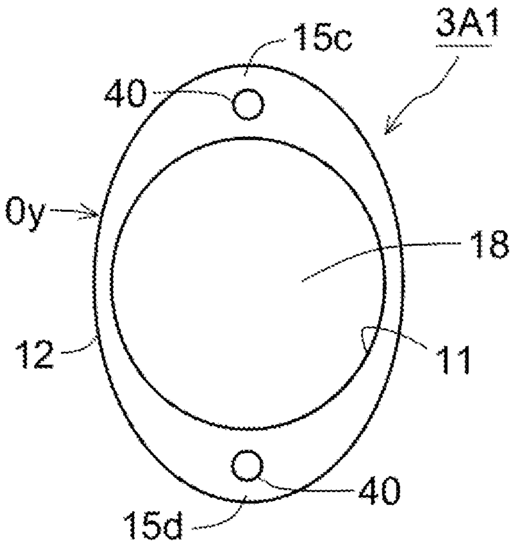
FIG. 15A is an overall plan view illustrating an endoscopic treatment portion traction member according to a twenty-fifth example.
Figure 15B:
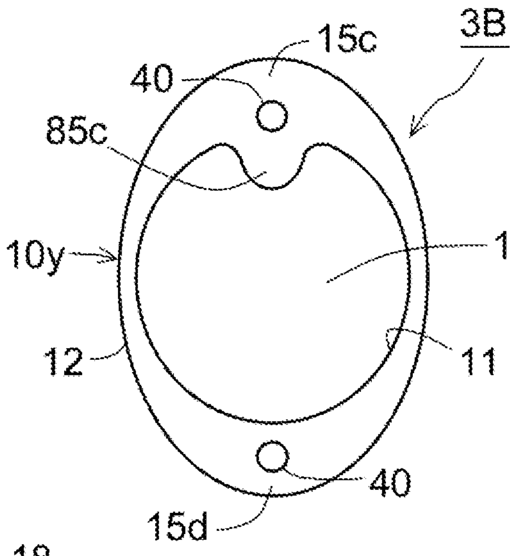
FIG. 15B is an overall plan view illustrating an endoscopic treatment portion traction member according to a twenty-sixth example.
Figure 15C:
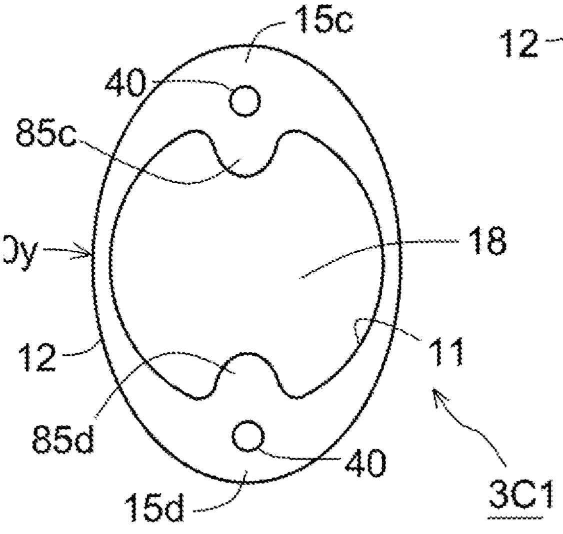
FIG. 15C is an overall plan view illustrating an endoscopic treatment portion traction member according to a twenty-seventh example.

FIG. 15A illustrates an endoscopic treatment portion traction member 3A1 according to the twenty-fifth example, FIG. 15B illustrates an endoscopic treatment portion traction member 3B1 according to the twenty-sixth example, and FIG. 15C illustrates an endoscopic treatment portion traction member 3C1 according to the twenty-seventh example. Even the endoscopic treatment portion traction members 3A1, 3B1, and 3C1 with oval-shaped annular bodies in which the widths of the outer tongues are extended are capable of accommodating both the gripping of the outer tongue 15 by the forceps 20 or the insertion of the forceps tip end 25 into the tongue pore 40.

Figure 16A:
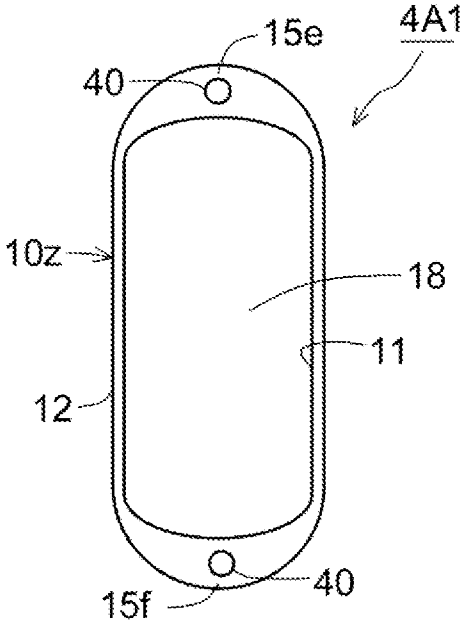
FIG. 16A is an overall plan view illustrating an endoscopic treatment portion traction member according to a twenty-eighth example.
Figure 16B:
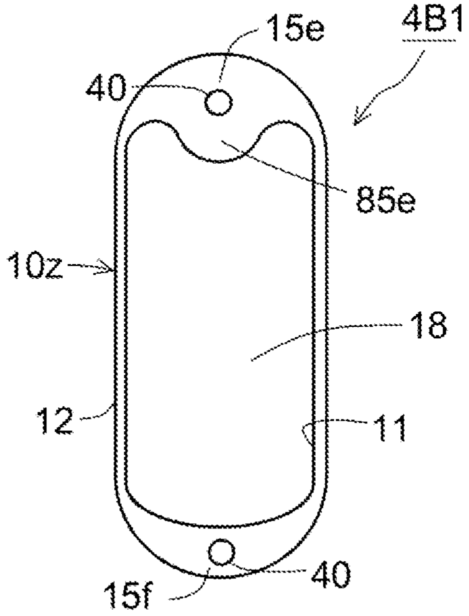
FIG. 16B is an overall plan view illustrating an endoscopic treatment portion traction member according to a twenty-ninth example.
Figure 16C:
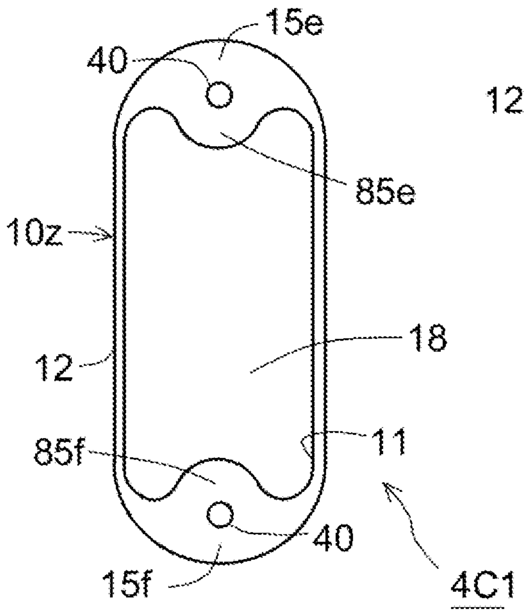
FIG. 16C is an overall plan view illustrating an endoscopic treatment portion traction member according to a thirtieth example.

FIG. 16A illustrates an endoscopic treatment portion traction member 4A1 according to the twenty-eighth example, FIG. 16B illustrates an endoscopic treatment portion traction member 4B1 according to the twenty-ninth example, and FIG. 16C illustrates an endoscopic treatment portion traction member 4C1 according to the thirtieth example. The modified oval-shaped endoscopic treatment portion traction members 4A1, 4B1, and 4C1 are capable of accommodating both the gripping of the outer tongue 15 by the forceps 20 or the insertion of the forceps tip end 25 into the tongue pore 40.

Figure 17A:
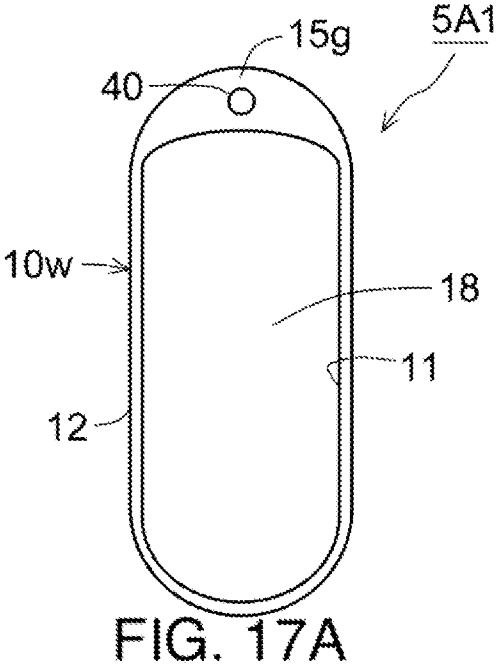
FIG. 17A is an overall plan view illustrating an endoscopic treatment portion traction member according to a thirty-first example.
Figure 17B:
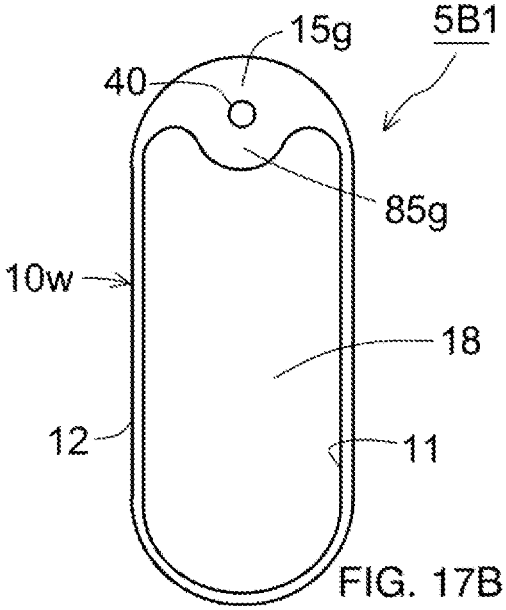
FIG. 17B is an overall plan view illustrating an endoscopic treatment portion traction member according to a thirty-second example.

FIG. 17A illustrates an endoscopic treatment portion traction member 5A1 according to the thirty-first example, and FIG. 17B illustrates an endoscopic treatment portion traction member 5B1 according to the thirty-second example. The oval-shaped endoscopic treatment portion traction members 5A1 and 5B1, which are deformed in the same manner as in FIGS. 16A to 16C, are capable of accommodating both the gripping of the outer tongue 15 by the forceps 20 or the insertion of the forceps tip end 25 into the tongue pore 40.

INDUSTRIAL APPLICABILITY

Our endoscopic treatment portion traction members have improved ease of use with endoscopic forceps in comparison to the existing traction members. Therefore, it is promising as a traction member for procedures such as endoscopic submucosal dissection.

INCORPORATION BY REFERENCE

This application is a continuation application of International Application No. PCT/JP2021/044793, filed on Dec. 6, 2021, which claims priority of Japanese (JP) Patent Application No. 2020-202679, filed on Dec. 7, 2020, the contents of which are hereby incorporated by reference in its entirety.

What is claimed is:

1. An endoscopic treatment portion traction member that is gripped by forceps to be inserted into an endoscope and then inserted into a body, and is fixed to a tissue to be resected and pulls the tissue from a surrounding tissue, the endoscopic treatment portion traction member comprising:

an annular body;

an outer tongue provided in a peripheral portion of the annular body and is gripped by the forceps; and an inner tongue provided on an inner circumferential portion of the annular body opposite the outer tongue;

wherein the endoscopic treatment portion traction member is formed from silicone resin as elastic resin, and wherein the annular body is circular in shape and a maximum length of the outer tongue is 1/10 to 6/10 of a diameter of the peripheral portion of the circular annular body, or, wherein the annular body is oval in shape and a maximum length of the outer tongue is 1/10 to 3/10 of a minor axis length of the peripheral portion of the oval-shaped annular body.

2. The endoscopic treatment portion traction member according to claim 1, wherein the outer tongue is provided at one or two locations in the peripheral portion of the annular body.

3. The endoscopic treatment portion traction member according to claim 2, wherein the outer tongue has a tapered portion.

4. The endoscopic treatment portion traction member according to claim 1, wherein the outer tongue has a tapered portion.

5. The endoscopic treatment portion traction member according to claim 1, wherein a tip end of the outer tongue is chamfered in a shape of a circular arc.

6. The endoscopic treatment portion traction member according to claim 1, wherein the annular body is circular in shape and a diameter of the peripheral portion of the annular body is 5 to 30 mm.

7. The endoscopic treatment portion traction member according to claim 1, wherein the outer tongue is formed with a tongue pore.

8. The endoscopic treatment portion traction member according to claim 1, wherein when the endoscopic treatment portion traction member is fixed to the tissue to be resected, the endoscopic treatment portion traction member is suspended via a clip secured to the tissue to be resected.

* * * * *